US008846075B2

(12) United States Patent
Jonsson et al.

(10) Patent No.: US 8,846,075 B2
(45) Date of Patent: Sep. 30, 2014

(54) COMPOSITION MATERIAL FOR TRANSMUCOSAL DELIVERY

(75) Inventors: Ingemar Jonsson, Helsingborg (SE);
Hans Henrik Lidgard, Lund (SE);
Gustaf Plym Forshell, Helsingborg (SE)

(73) Assignee: Magle Holding AB, Lund (SE)

( * ) Notice: Subject to any disclaimer, the term of this patent is extended or adjusted under 35 U.S.C. 154(b) by 1460 days.

(21) Appl. No.: 10/543,856

(22) PCT Filed: Jan. 23, 2004

(86) PCT No.: PCT/SE2004/000091
§ 371 (c)(1),
(2), (4) Date: Mar. 15, 2006

(87) PCT Pub. No.: WO2004/064811
PCT Pub. Date: Aug. 5, 2004

(65) Prior Publication Data
US 2006/0147498 A1   Jul. 6, 2006

Related U.S. Application Data

(60) Provisional application No. 60/456,474, filed on Mar. 24, 2003.

(30) Foreign Application Priority Data

Jan. 24, 2003   (SE) ........................................ 0300187
Nov. 7, 2003    (SE) ........................................ 0302947

(51) Int. Cl.
  *A61K 9/28*   (2006.01)
  *A61K 9/00*   (2006.01)
  *A61K 9/20*   (2006.01)
  *A61K 9/68*   (2006.01)
(52) U.S. Cl.
  CPC .............. *A61K 9/0058* (2013.01); *A61K 9/205* (2013.01); *A61K 9/009* (2013.01); *A61K 9/006* (2013.01); *A61K 9/2054* (2013.01)
  USPC .......................................... 424/441; 424/400

(58) Field of Classification Search
  CPC ... A61K 31/00; A61K 9/2054; A61K 9/0056; A61K 9/006; A61K 47/10; A61K 9/0058; A61K 9/205; A61K 9/009
  USPC ................................................... 424/441, 400
  See application file for complete search history.

(56) References Cited

U.S. PATENT DOCUMENTS 2,776,916 A * 1/1957 Ericsson ..................... 131/352
3,757,798 A * 9/1973 Lambert ..................... 131/270
(Continued)

FOREIGN PATENT DOCUMENTS

CA    2 332 559    1/2000
EP    0250187     12/1987
(Continued)

OTHER PUBLICATIONS

Bokelman, Gordon H. et al. "Fractionation of Bright Tobacco" J. Agric. Food Chem. 1983, 31, 397-901.*
(Continued)

*Primary Examiner* — Aradhana Sasan
(74) *Attorney, Agent, or Firm* — Alston & Bird LLP (57) ABSTRACT

The invention refers to a composition material that is intended for rapid transmucosal delivery in the mouth of a biologically active substance when in contact with saliva. The composition material comprises at least one ionic carbohydrate, having at least one biologically active substance ionically bound thereto, and at least one wetable non-soluble polymeric carbohydrate. The invention also refers to a method of preparing the composition material, which comprises the steps of: (a) providing a mixture of the at least one biologically active substance and at least one ionic carbohydrate in a solvent having a permissive pH for ionic bonding of the at least one biologically active substance to the at least one ionic carbohydrate; (b) mixing the mixture in the solvent for a period that is sufficient for allowing the ionic bonding to take place; and (c) recovering the mixture from the solvent.

24 Claims, 2 Drawing Sheets

(56) References Cited

U.S. PATENT DOCUMENTS

| | | | | |
|---|---|---|---|---|
| 3,830,404 | A | * | 8/1974 | Frazer .................. 222/78 |
| 3,845,217 | A | | 10/1974 | Femo et al. |
| 3,869,406 | A | * | 3/1975 | Matsukawa et al. ..... 427/213.33 |
| 4,029,758 | A | * | 6/1977 | Mlodozeniec et al. ....... 424/452 |
| 4,066,556 | A | * | 1/1978 | Vaillancourt .................. 210/448 |
| 4,369,172 | A | | 1/1983 | Schor et al. |
| 4,783,239 | A | * | 11/1988 | Rich .................. 162/91 |
| 4,795,644 | A | * | 1/1989 | Zentner .................. 424/468 |
| 4,849,246 | A | * | 7/1989 | Schmidt .................. 427/2.21 |
| 4,907,605 | A | * | 3/1990 | Ray et al. .................. 131/270 |
| 5,167,244 | A | | 12/1992 | Kjerstad |
| 5,192,802 | A | * | 3/1993 | Rencher .................. 514/535 |
| 5,225,431 | A | * | 7/1993 | Robertson et al. ............ 514/389 |
| 5,400,808 | A | | 3/1995 | Turner et al. |
| 5,424,289 | A | * | 6/1995 | Yang et al. .................. 514/12 |
| 5,516,530 | A | * | 5/1996 | Lo et al. .................. 424/473 |
| 5,599,554 | A | * | 2/1997 | Majeti .................. 424/448 |
| 5,656,284 | A | | 8/1997 | Balkin |
| 5,939,100 | A | | 8/1999 | Albrechtsen et al. |
| 6,432,440 | B1 | * | 8/2002 | Watts et al. .................. 424/434 |
| 2001/0022964 | A1 | * | 9/2001 | Leung et al. .................. 424/49 |
| 2003/0068376 | A1 | * | 4/2003 | Chen et al. .................. 424/484 |
| 2004/0191322 | A1 | | 9/2004 | Hansson .................. 424/489 |
| 2005/0061339 | A1 | | 3/2005 | Hansson et al. |

FOREIGN PATENT DOCUMENTS

| | | |
|---|---|---|
| EP | 1 637 154 A2 | 3/2006 |
| GB | 1 401 585 | 7/1975 |
| JP | 03-209327 A | 9/1991 |
| JP | H06502622 A | 3/1994 |
| JP | 9-286729 A | 11/1997 |
| JP | 2000-504028 A | 4/2000 |
| JP | 2002-515086 A | 5/2002 |
| JP | 2002-322088 A | 11/2002 |
| WO | WO-91/09599 A1 | 7/1991 |
| WO | WO 92/01445 A1 | 2/1992 |
| WO | WO 95/12399 A1 | 5/1995 |
| WO | WO 97/42941 A2 | 11/1997 |
| WO | WO 98/08550 A1 | 3/1998 |
| WO | WO 00/02574 | 1/2000 |
| WO | WO 00/10536 | 3/2000 |
| WO | WO 01/49292 A1 | 7/2001 |
| WO | WO-01/89476 A1 | 11/2001 |
| WO | WO-02/085119 A1 | 10/2002 |
| WO | WO-02/085334 A1 | 10/2002 |
| WO | WO 02/102357 A1 | 12/2002 |
| WO | WO 03/053175 A2 | 7/2003 |
| WO | WO-2004/054551 A1 | 7/2004 |

OTHER PUBLICATIONS

Chamberlain, William J. et al. "Chemical Composition of Nonsmoking Tobacco Products" J. Agric. Food Chem. 1988, 36, 48-50.*

International Search Report for PCT/SE2004/000091 dated May 6, 2004.

Mihranyan, et al., "Sorption of Nicotine to Cellulose Powders," *European Journal of Pharmaceutical Sciences*, 2004, vol. 22, pp. 279-286.

Turquois, et al., "Extraction of Highly Gelling Pectic Substances from Sugar Beet Pulp and Potato Pulp: Influence of Extrinsic Parameters on Their Gelling Properties," *Food Hydrocolloids*, 1999, vol. 13, pp. 255-262.

Written Opinion for Application No. PCT/SE2004/000091 dated Dec. 5, 2004.

* cited by examiner

Fig. 2

COMPOSITION MATERIAL FOR TRANSMUCOSAL DELIVERY

CROSS REFERENCE TO RELATED APPLICATIONS

This application is a national phase entry of International Application No. PCT/SE2004/000091, filed Jan. 23, 2004, which claims priority to Sweden Application No. 0300187-2, filed Jan. 24, 2003, U.S. Provisional Application No. 60/456,474, filed Mar. 24, 2003, and Sweden Application No. 0302947-7 filed Nov. 7, 2003, each of which is hereby incorporated herein in its entirety by reference.

FIELD

The invention refers to a composition material for transmucosal delivery. More precisely, the invention refers to a composition material for a highly efficient transmucosal delivery in the mouth of biologically active substance(s), a pouch containing the composition material as well as an envelope for the composition material or the pouch.

BACKGROUND

In recent years transmucosal delivery systems for biologically active substances have been studied more and more extensively. These systems are believed to have advantages that are not found with oral, transdermal or even intravenous delivery systems for such substances. Active agents, which require inconvenient intravenous administration due to poor oral bioavailability, are particular candidates for delivery via the oral mucosal tissues.

The buccal region of the mouth in the upper gum and inside cheek region provides a barrier to delivery that is more permeable than the skin itself and tends to be less variable between individuals. The membranes of the mouth are thin and permeable. The buccal mucosa is less sensitive to irritation than the nasal mucosa, which makes buccal delivery more acceptable to the patient. This is especially evident when the patient carries a virus infection which often—if followed by swelling and large secretions of the nasal mucosa—can effect the nasal transmucosal delivery with accompanying uncertainty of delivered dose. This makes buccal transmucosal delivery particularly attractive.

Another advantage for using this route is to avoid the first pass metabolism of the substance in the liver. Furthermore, the highly acidic conditions of the stomach and effects of proteases and their zymogens are avoided. The latter act in the intestines and are well known to inactivate and degrade different biologically active substances.

The main advantage of transmucosal delivery, however, is that biologically active substances can be absorbed directly into the bloodstream, allowing for rapid uptake of the substance into the body. Furthermore, by transmucosal delivery to the blood stream no active substance is lost due to first-pass liver metabolism. Thus, transmucosal delivery system provides quick passage through the mucous membranes of the mouth for faster absorption.

The buccal mucosa has a large area of smooth muscle and relatively immobile mucosa. This makes it a desirable region for transmucosal delivery systems. Accordingly, the buccal mucosa is considered more suitable for sustained delivery applications as well as delivery of less permeable molecules.

However, a rapid release of a biologically active substance is many times more desirable immediately after its administration. For example, a rapid release of the active substance is of crucial importance particularly with analgesics in order to achieve a rapid onset of the pain-relieving action. Likewise, people with sleeping disorders and those who are suffering from nausea need a fast onset of action when a biologically active substance is administrated. Another biologically active substance is nicotine, the effect of which people prefer to be instant when taken.

A frequently used alternative for smoking tobacco, especially in the Scandinavian countries and in the USA, has been the habit of using snuff made from tobacco and alternatively and specifically in the US, chewing tobacco. Chewing tobacco consists of the tobacco leaf with the stem removed. It is produced in the form of long strands of tobacco. The chewing tobacco is also available in small pouches that can be placed between the cheek and gum. Snuff, on the other hand, consists of the entire tobacco leaf, which is dried and granulated or finely cut. Various sweeteners and flavorings are added to these smokeless tobacco products.

Although some people prefer to sniff the snuff, many consumers takes a pinch of snuff (2-3 ml) from a can with moist powder and place it between the lip or cheek and gum and suck on it. The wet snuff is also produced as portion packed pouches that are placed likewise. While enjoying the texture of the fine grain tobacco, the nicotine is leached from the tobacco and delivered to the mucosa of the user.

Portion packed snuff is considered less damaging to the buccal mucosa than loose snuff. However, individuals consuming large amounts of snuff exhibit irritation of the overexposed mucosa and signs of peridontitis have been reported.

In addition, the Swedish tradition of taking wet snuff results in what many people experience as a strong nasty smell, which some people seem to be sensitive for. Furthermore, a pinch or a portion of snuff results in a bulging facial appearance which may look ill-mannered. Moreover, the snuff has a tendency to leak a stained liquid from the mouth during prolonged use. It may also leave unattractive tobacco spots when subsequently removed and thrown away in toilets, washbowls etc.

It is also well-known that chewing tobacco and snuff contain potentially harmful substances, such as volatile and nonvolatile nitrosamines, tobacco-specific N-nitrosamines, polynuclear aromatic hydrocarbons, and polonium-210. Thus, snuff consumers may be exposed to hazardous chemicals.

A number of tobacco substitutes have been developed and introduced to the market over the years as medical products, i.e. nicotine smoking deterrents. These products are used in nicotine replacement therapies, such as transdermal nicotine patches or chewing gums.

Nicotine patches, i.e. transdermal nicotine systems, provide a measured relatively slowly transferred dose of nicotine through the skin. The nicotine gum is a relatively faster acting form of replacement that acts through the mucous membrane of the mouth when the gum is chewed. Chewing stimulates secretion of saliva and the nicotine containing saliva causes irritation of the throat and when swallowed nicotine is lost due to first-pass liver metabolism. In addition, prolonged chewing results in a jaw discomfort, chewing gums are not always socially accepted, and the chewing in itself is considered impolite in certain cultures.

A nicotine nasal spray delivers the nicotine more quickly to the bloodstream as it is absorbed through the nose. The nasal spray is said to immediately relieve withdrawal symptoms and nicotine cravings. Such a therapy is available only by prescription. Nicotine inhalers were introduced in 1998 and are now available over the counter (OTC) in many countries.

WO 95/12399 shows a powdery pharmaceutical compositions that is especially intended for nasal administration. The compositions comprise nicotine and starch microspheres and show increased bioavailability of the drug when administered nasally.

In WO 91/09599 a smoking substitute composition is shown, which is intended for nasal, sub-lingual or buccal administration. The composition contains nicotine in the form of an inclusion complex with a cyclodextrin compound. This inclusion of nicotine in a cyclodextrin complex reflects the tendency of nicotine to evaporate if not bound or enclosed. The composition of WO 91/09599 also comprises excipients accepted for food or pharmaceutical use.

U.S. Pat. No. 4,369,172 shows a compressed medicinal solid unit dosage form which comprises a medicament and, as carrier, hydroxypropyl methylcellulose, ethylcellulose and/or sodium carboxymethylcellulose. The dosage forms are said to have a more prolonged release pattern than prior products of this type.

An oral nicotine dispenser is shown in U.S. Pat. No. 4,907,605, which comprises nicotine and a water insoluble polymeric substance formed of strips. The polymeric substance can be paper or cellulose, such as cellulose acetate, polyethylene, or polypropylene. The dispenser can be chewed or placed in the mouth to slowly release the sorbed nicotine into an oral environment.

Likewise, a slow release composition is shown in U.S. Pat. No. 3,845,217, which comprises a gum base, a buffering agent, and a complex containing nicotine bound to a synthetic cation exchanger. The complex is easy to handle and minimizes the personal risks during manufacturing, when it also acts as a lubricant.

The object of the invention is to provide a safe composition material that is adapted for rapid as well as slow release of a biologically active substance.

SUMMARY

According to the invention a method is provided for preparing a composition material for rapid and direct transmucosal delivery of a biologically active substance, when in contact with a body liquid. The biologically active substance can for example be absorbed by the inner lining of the mouth, thereby mimicking the pharmacokinetics of parenteral administration (i.e. injection).

The method comprises the steps of:
(a) providing a mixture of the biologically active substance and at least one ionic carbohydrate in a solvent having a permissive pH for ionic bonding of the biologically active substance to the at least one ionic carbohydrate;
(b) mixing the mixture in the solvent for a period that is sufficient for allowing the ionic bonding to take place; and
(c) recovering the mixture from the solvent.

DETAILED DESCRIPTION

In order to obtain a mixture, the biologically active substance can first be added to the ionic carbohydrate in the solvent or vice versa. The mixing is then performed for a period that is sufficient for ionic binding of the components. The solvent is of course dependent on the nature of the biologically active substance and can be a volatile hydrophilic solvent. Preferred solvents are those which are volatile at low temperatures, whereby the potential damaging effect on the biologically active substance is reduced. Preferably, the solvent is ethanol, water, or a mixture thereof.

The composition material according to the invention is intended to be used in a wide variety of combinations of carbohydrates, whereby the properties of each individual component in the material is utilized in order to obtain efficient binding and suitable release properties to the mucosa in the mouth, i.e. controlled release as rapid as well as slow release.

The ionic carbohydrate can be an ionic polymeric carbohydrate or an ionic oligomeric carbohydrate. The oligomeric carbohydrate can be an oligomer of an ionic polymeric carbohydrate or a synthetic carbohydrate. The ionic polymeric as well as the ionic oligomeric carbohydrate can be cross-linked. Preferably, the ionic polymeric carbohydrate is of natural origin.

If anionic, the carbohydrate can be a natural organic cation exchanger. Examples of highly anionic natural polymeric carbohydrates are carrageenan, alginate, fully demethylated pectin (polygalacturonic acid), heparine, hyaluronic acid, and chondroitin sulfate, which are useful for the ionic bonding of a biologically active substance according to the invention. Weaker cation exchangers are agar, furcellaran, xanthan, gum ghatti, gum karaya, gum arabicum as well as less demethylated pectin. Of course, the anionic potency of the polymeric carbohydrate depends on the cationic strength of the biologically active substance to be ionically bound. Pectin and alginate are preferred, since they can be obtained negatively charged over a large pH range, typically pH 2-9, which is most frequently manifested by free $COO^-$-groups.

The anionic carbohydrate can also be a chemically modified, i.e. a derivatized natural polymeric carbohydrate. Examples of such carbohydrates are well-known within the art, e.g. carboxymethyl cellulose, cellulose sulfate, and sulfopropyl cellulose. Alternatively, dextran and starch can be derivatized in a similar way.

In dependence of the nature of the biologically active substance to be ionically bound the ionic polymeric carbohydrate can also be a cationic natural polymeric carbohydrate, for example chitosan.

Likewise, the cationic natural polymeric carbohydrate can be a cationically derivatized natural polymeric carbohydrate, such as a diethylaminoethyl or diethyl(2-hydroxypropyl)amminoethyl derivatized natural polymeric carbohydrate. Suitable natural polymeric carbohydrates to be cationically derivatized are cellulose and starch.

In order to achieve binding to a negatively charged carbohydrate the biologically active substance has to be positively charged, i.e. a permissive pH for ionic bonding must be obtained. If the potential biologically active substance has a $pK_a$ that is above the lower pH range of the anionic carbohydrate, a suitable pH for ionic binding must be established. For example, if nicotine, which has $pK_a$ of 8.2, is used as a biologically active substance, a suitable pH for binding of about pH 7.0 must be reached.

A corresponding shift in pH may be necessary if a cationic carbohydrate is used to bind a biologically active substance of opposite charge.

In order to obtain a permissive pH for ionic bonding of the biologically active substance to the ionic carbohydrate a suitable amount of a pH controlling agent can be included in the mixture of the inventive method (step a'). Preferably, the pH controlling agent is a volatile acid, such as acetic acid, formic acid etc. Other suitable pH controlling agents are citric acid and phosphate buffers.

The pH controlling agent can also be an ionic carbohydrate as described above. In this case, the ionic carbohydrate used as pH controlling agent should have a charge opposite that used for the binding of the biologically active substance.

After binding, the mixture is recovered from the solvent. This is accomplished in dependence of the nature of the ionic carbohydrate and the biologically active substance ionically bound thereto. Different methods known within the art can be applied, for example centrifugation and subsequent lyophilization. However, it is preferred that the mixture is evaporated to dryness. In this connection the expressions dryness or dry means a water content of less than 15%, preferably less than 10%, residual water mainly being bound water.

With this procedure both the solvent and the volatile acid will evaporate, leaving the biologically active substance ionically bound to the ionic carbohydrate.

It is preferred that at least one wetable non-soluble polymeric the mixture further comprises carbohydrate, the nature of which is principally non-ionic. Thus, the inventive method further comprises the step (a") of adding at least one wetable non-soluble polymeric carbohydrate to the mixture.

In this connection the expression non-soluble means that the polymeric carbohydrate has an intact matrix and is not dissolute within at least 1 h. A prolonged dissolution by chemically crosslinking the polymeric carbohydrate, e.g. by means of epichloride.

The expressions wetable or wetted refers to that the polymeric carbohydrate is wetable, liquid absorbing and/or swellable in contact with moisture and liquid, such as the solvent when prepared or the body liquid during leaching, e.g. in contact with saliva. Most fibrous carbohydrates possess these properties.

By utilizing a wetable non-soluble polymeric carbohydrate, the biologically active substance—ionically bound to the ionic carbohydrate—can be included in the composition material structure. It is believed that when the composition material is prepared, the material draws the solvent for the biologically active substance through the pores formed by the intermingled fibres of the polymeric carbohydrate as well as the ionic carbohydrate with its bound substance.

Ionic carbohydrates—chemically modified or not—can be used with varying number of acidic groups independent of their solubility since they are intermixed with the wetable non-soluble polymeric carbohydrate.

The wetable non-soluble polymeric carbohydrate can be a natural carbohydrate such as cellulose, hemicellulose, dextran, agarose, or starch etc. It is an advantage if the natural carbohydrate is derived from insoluble dietary fibers, such as those from potatoes, rice, maize, sugar beat, and soy.

Other fibrous cellulose materials suitable as a polymeric carbohydrate co-carrier for the ionically bound biologically active substance, are obtained from wood and cotton. Examples of commercial materials are cellulose wadding (e.g. Cellucotton® from Kimberly-Clark), micro-crystalline cellulose (e.g. AviCell™ from FMC), and filter paper materials (e.g. from Whatman). Modified cellulose fibers can also be used in this connection, for example derivatized cotton.

The wetable non-soluble polymeric carbohydrate is usually used as a non-ionic material. However, it can in itself have an ion exchange effect, although minor. Examples of such carbohydrates are agar-agar, potato starch and shoti starch.

Likewise, the sorbing capacity of different polymeric carbohydrates can be utilized in dependence of the biologically active substance used. The release of the substance can be further controlled not only by the small ion exchange properties of different non-soluble polymeric carbohydrates but also but also by their ability to adsorb, absorb, or non-specifically bind the biologically active substance.

Further ethanol and/or water can with advantage be added to the mixture in order to control the porous structure and the texture of the final composition material.

A suitable mixture of carbohydrates to be used in the present invention is a mixture of 17-19% pectin, 27-30% cellulose, and 20-24% hemicellulose, which can be purchased as a fibre-rich residual product from potato starch. This fibrous material also contains 12-15% potato starch.

Figure 2:
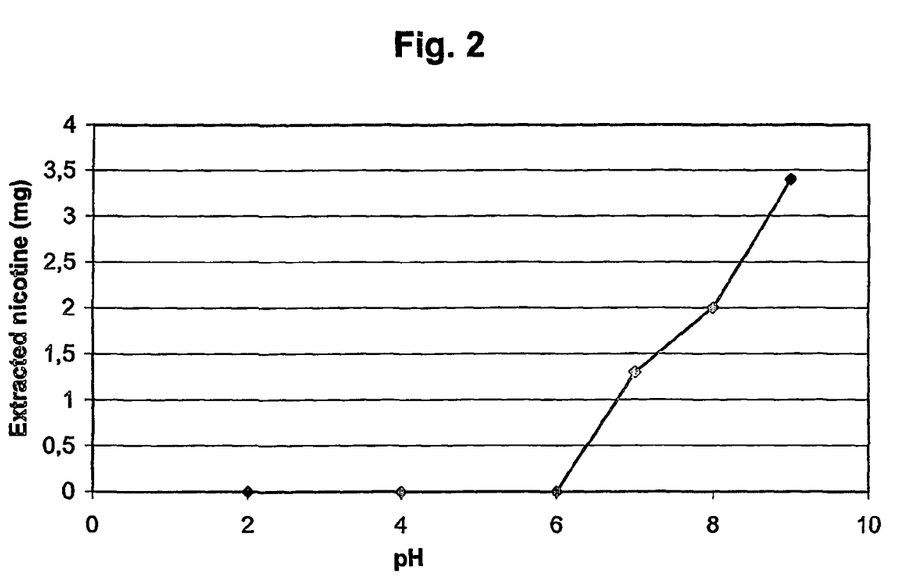
FIG. 2 illustrates the results of the nicotine extraction of Example 18.

The binding and release of biologically active substance(s) to this preferred material depends on several parameters. An ionic/non-specific binding and diffusion limitation is believed to exert controlled release of the substance(s) sorbed to/in the preferred material. One reason for controlled release can be accounted for a slow swelling of the product releasing active substance bound deep in the composite material (c.f. FIG. 2).

The composite form of dietary fibres combining e.g. pectin cellulose, and hemicellulose etc., having a particle size distribution of <0.1 mm to 2 mm, or sieved fractions thereof, explain the unique combination of a quick onset and a controlled release which can be amplified by the addition of a pH controlling agent and/or various degrees of cross linking the material and/or the relative amount of active substance per mg added composite material. This is unique to buccal formulations.

In addition, one or several penetration enhancers, as known in the art, may be included in the mixture. These compounds assist in speeding up the rate of transmucosal delivery in dependence on the nature of the biologically active substance, for example its lipophilic or hydrophilic characteristics, size and molecular weight. Examples of enhancers are bile acids, dihydrofusidates, ionic and non-ionic surfactants, as well as chelating agents.

A dry composition material can according to the invention be recovered by means of the inventive method, with or without a wetable non-soluble polymeric carbohydrate.

In principle, all biologically active substances having an isoelectric point between pH 4 and 9 can be used in the inventive composition material. Suitable biologically active substances are proteins, peptides, alkaloids, drugs for the treatment of migraine, hypnotics, sedatives, local anaesthetics, analgesics, and drugs for the treatment of psychiatric disorders. Stimulating agents can also be used. Another useful substance is nitroglycerine.

Examples of suitable peptides are desmopressin, lypressin, oxytocin, nafarelin, buserelin, and growth hormones.

Examples of suitable alkaloids are nicotine, cotinine, and lobeline, or a derivative or a salt thereof, as well as caffeine. Ergot alkaloids and $5HT_1$-receptor agonists can be used as drugs for the treatment of migraine, e.g. zolmitriptanes.

The composition material according to the invention provides a dosage form that promotes effective absorption through the lining of the oral cavity. A direct absorption and a rapid onset of a biologically active substance is achieved. For example, it can be used in connection with sea sickness, sleep disorders and when antidotes are urgently required.

The biologically active substance may be absorbed systemically or may exert a local action on adjacent tissue structures. For example, an anaesthetic can be administered locally for dental use by means of the inventive composition material instead of being injected. The local anaesthetic can be lidocaine or mepivacaine.

The free biologically active substance may in itself have a pH regulating effect by adding buffering capacity and stabilizing the pH in e.g. the saliva. However, it is preferred that the inventive method further comprises the step (c') of adding a pH controlling agent to the recovered mixture. When the mixture is dry, the pH controlling agent should of course also be dry. A pH controlling agent is included in the evaporated mixture, or slurry, in order to attain a high pH for an extended period of time, i.e. more than 1 h, when the dry composition material is contacting water.

It is preferred, especially when an anionic carbohydrate is used, that the pH controlling agent is a biologically compatible buffer having a $pK_a$ that is higher than the pH of the body liquid, such as the pH of saliva. A stable pH for desorption from the ionic carbohydrate, i.e. similar or above the $pK_a$ of the biologically active substance, can for example be achieved by the addition of a carbonate or phosphate buffer. Ammonia can also be used. If a lower pH is applicable, acetic acid or citric acid can be an alternative.

Advantageous pH changes are obtained with the inventive composition material. For example, when an anionic polymeric carbohydrate is used to bind a biologically active substance of opposite charge, a low pH is provided initially, below the $pK_a$ of the biologically active substance. At this point the weak base will dissolve and bind to the anionic polymeric carbohydrate because the ionized form predominates. When the pH then is increased to a high pH, above the $pK_a$ of the biologically active substance and well above the pH of the body liquid, the ionized substance will be converted to its un-ionized form and be desorbed from the material. This form will predominate, which is more permeable to biological tissues, the repulsive forces of the membranes high net negative charge being abolished. Thus, the release of the biologically active substance, and its uptake through the mucosa, can be controlled by selecting the proportions of the pH controlling agent.

In addition the invention provides a composition material for transmucosal rapid delivery of a biologically active substance. The inventive composition material comprises at least one ionic carbohydrate, to which the biologically active substance is ionically bound, and at least one wetable non-soluble polymeric carbohydrate. When contacting saliva, the composition material should have a pH between 4 and 9, preferably between 5.4 and 8.2.

The composition material is suitable for dosage forms that in the mouth rapidly deliver biologically active substances transmucosally. It can be placed under the lip, or between cheek and gum, i.e. to be delivered by means of leaching to the buccal mucosa of the lips and gums.

The invention utilizes the main reason for transmucosal delivery in the mouth of a biologically active substance, i.e. its rapid administration. The inventive composition material is intended to be used for controlled-release in the sense of rapid instant or immediate release as well as for sustained-release or extended-release. The composition material should hold a quantity of biologically active substance, which is sufficient to provide an effective dose within a short time, preferably within seconds or minutes.

The composition material is intended to be sized and to be held in the mouth between a lip mucosa and a gingiva mucosa, the biologically active substance being released at least bi-directionally in generally opposite directions to both of the opposed lip mucosa and gingiva mucosa. The material can be placed on the gum between the lip or cheek on either side of the mouth. Once in place, the biologically active substance is rapidly released to the mucous membrane of the mouth for local application or entering into the blood stream. This means that the biologically active substance, contained in the composition material, is delivered by means of leaching from more than one side or surface of the same, i.e. in generally opposite directions. The bi-directional delivery to the opposed mucosa increases the speed of delivery.

The composition material is flexible enough both as initially dry and when wetted and/or swollen to adapt to the tissue of the mouth in intimate contact with the mucosal membrane(s) within the buccal cavity. The material can be applied without significant pressure. It remains between the lip mucosa and the opposed gingiva mucosa solely by virtue of its size and the fit. In this way it can comfortably remain between a lip mucosa and a gingiva mucosa for long periods of time without being adhered and without substantial movement and risk of accidental swallowing, while in contact with the mucosa and sheltered from contact with the large mounts of saliva present elsewhere in the mouth.

The composition material for transmucosal rapid delivery under the lip of a biologically active substance by means of leaching can be in the form of a sheet, a disc, an oval, a kidney shape, a cylinder, strips, discrete pieces, or as granulates. The latter three forms can preferably be packed in pouches made of a flexible liquid permeable material. Other forms can be used in chewing gums as a delivery system for biologically active substances. Tablets, pills, capsules, and lozenges can also be used for delivery within the mouth.

A general benefit of the locating of the pouch/tablet etc to the gingival fold of the mouth is that there is very limited diffusion of active biological substance(s) to the other parts of the buccal region. This is especially evident when they are compared with for example nicotine chewing gums and lozenges, a large portion of the active substance diffusing into the saliva and is swallowed and not available to the buccal mucosa. This is easily evident by the strong taste of for example nicotine in the mouth while chewing.

When for example in the form of a sheet, preferred shapes include strips, but other shapes can also be used, which conform to a shape in the mouth. The length can be 5-40 mm, preferably 15-30 mm. A suitable size is from 1×2 mm to 10×20 mm. The thickness can be less than 5 mm, such as between 0.5 and 3 mm, preferably between 1 and 2 mm. Of course, the length and the thickness can be varied in accordance with the substance to be rapidly released. Alternatively, the composition material is cut pieces of a fine mesh gauze, which when packed form a fine resilient network suitable for diffusion.

The composition material as a sheet, or a pouch containing the same, is prepared to have a thickness and flexural stiffness which enables it to conform to the contoured surfaces of the gum of the consumer and to adjacent soft tissue. The composition material according to the invention utilizes the high moisture content of mucosal tissues, the difficulties of adherence of solid devices to the same being avoided. The inventive material is adapted to generate a rapid release of the biologically active substance when in contact with the body liquid. The substance may be absorbed systemically or it may exert its effect locally on adjacent tissue.

A sheet can be manufactured from a composition material comprising pectin, cellulose, hemicellulose, and bound biologically active substance, starch being used as a binder. Likewise, thin films of alginate can be produced and for example laminated to cellulose sheets. In this case the alginate film with bound biologically active substance will—during its dissolution in contact with water—be held in place by the cellulose material, a more rapid release being obtained.

A pouch containing the composition material according to the invention is intended to fit into the gingival fold of the mouth. A non-woven fabric is preferably used as a package material for such pouches. Thus, they are similar to small tea-bags and are packed with 0.05-2 g (dry weight), preferably 0.05-1.0 g, of composition material having the biologically active substance ionically bound therein. It is preferred that the package material is a "non woven fleece" of polycarbonate, 25 g/m$^3$, without coating, which is approved for food product applications. The non-woven fabric can be used as a bonding agent for sealing. Another suitable flexible liquid permeable material is made of viscose rayon (cellulose xanthate), a material that also can be heat-sealed. Longfibre cellulose non-woven materials, including a heat weldable binder, acrylic polymers, and Nylon® can also be used.

By providing the biologically active substance bound to a matrix in the form an ionic carbohydrate and in contact with a wetable polymeric carbohydrate, the contact of the substance with moisture as well as ambient oxygen and light is restricted, which prevents its deterioration and prolongs its shelf live.

When storing the composition material according to the invention, a vapor barrier is needed only to prevent it from contact with oxygen, moisture or water. However, the volatilization of any aroma compounds therein can also be prevented. Enveloped in the final product, such ingredients will be evenly distributed within the material. Preferably, a pouch is used, which is made of a suitable barrier material. Suitable barrier materials are well known to the skilled man and they can for example be made of an aluminium foil, a polyamide or ethylene vinyl alcohol film, or a film of an acrylonitrile copolymer, e.g. Barex® from BP Chemical, alone or in combinations. Before sealing an inert gas, e.g. nitrogen, can be added in order to increase the shelf-life of the contents. The envelope is then sealed, for example by means of heat welding of the acrylonitrile copolymer to aluminium when a Barex® coated envelope is used.

According to the invention, a low cost commercial composition material is provided, which is comfortable to wear and which can rapidly deliver a sufficient amount of a biologically active substance with good contact for optimal delivery. The non-bulky active composition material permits the wearer to use it during social discourse without interfering with the wearer's speech or appearance.

A useful test substance for the application of the inventive composition material is nicotine. When nicotine is used, a suitable quantity corresponds to a nicotine content of a portion (dose) between 0.05 and 15 mg, preferably between 0.05 and 6 mg, per dose, small doses being stimulating and large doses being relaxing.

It is also possible to supply such a smokeless tobacco substitute material with an aroma compound. Suitable compounds are those exhibiting mint, licorice, vanilla, strawberry, cranberry, raspberry, coffee, mocha, chocolate, eucalyptus, citrus, tar, and tobacco aromas. Other additives can also be included, such as liquor aromas (e.g. whiskey) as well as honey, rum, menthol, peppermint oil, camphor, attar of roses, and oil of cloves. The aroma compounds are preferably added as a dry powder. They can also be dried onto the wetable non-soluble polymeric carbohydrates.

When the biologically active substance is nicotine, an alternative smokeless tobacco substitute material, is provided, which

- can be used in connection with curing nicotine addiction;
- has a quick onset, similar to smoking or nasal administration, and a long term effect;
- reduces the risk of tobacco exposure by avoiding the thousands of questionable substances that are found in tobacco;
- does not give off strong nasty smell, but is sufficiently bitter in order to prevent consumption by children but not by adults;
- can be used where smoking is impolite, not possible or not allowed;
- is much more convenient to handle than when smoking cigarettes, no ashes or fumes being obtained;
- is a more socially accepted alternative and which can be manufactured very thin in order to reduce the visual effect on the face of the user;
- does not leak liquid when used and which is much easier disposed off without subsequent cleaning;
- exhibits a perception of touch similar to real snuff;
- is less elaborate to handle in comparison to traditional snuff; and
- is a cleaner form of substitute material than snuff and delivers lower doses of nicotine in order to satisfy the consumer.

EXAMPLES

Example 1

Pouches comprising 2 mg nicotine, buffered to pH 7.0.

A non woven polycarbonate fibre tube, 12 mm (in diam.)× 24 mm and a pore size of about 250 µm was heat welded in one end. The adsorbent used was the preferred material comprising 17-19% pectin, 27-30% cellulose, 20-24% hemicellulose. This material, 100 mg, was added and the other end was heat welded. A nicotine solution (pH 7, 20 µl), containing 100 mg nicotine/ml, was then added through the web and was allowed to disperse for 2 min, which resulted in a pouch dose of 2 mg.

The so ready pouch was then packed in an aluminium Barex® coated envelope that in turn also was heat welded to prevent nicotine loss.

The envelopes were furnished with a small cut in the side outside the weld to facilitate opening.

To determine the nicotine content pouches were made alkaline with sodium hydroxide and extracted with methyl tert-butyl ether and assayed for nicotine by gas chromatography/flame ionization detection.

Example 2

Pouches comprising 4 mg nicotine, no buffering capacity beside nicotine itself, pH≈8.0.

To 1.840 g of the preferred material, 160 mg pure nicotine dissolved in 25 ml ethanol, was added and well mixed in a vacuum E-flask. The flask was heated to 40 C under vacuum and the ethanol driven off. Full loss of ethanol was controlled by weight.

A non woven acrylic fibre tube, 12 mm (in diam.)×24 mm and a pore size of about 250 µm was heat welded in one end. The dry adsorbent, 50 mg, with bound nicotine was added and the remaining open end of the pouch was heat welded. Finally the pouches were packed as in Example 1.

Example 3

Pouches comprising 4 mg nicotine, buffered to about pH 8.3.

To 1.640 g of the preferred material 160 mg pure nicotine, dissolved in 25 ml EtOH, was added and well mixed in a vacuum E-flask. The flask was heated to 40 C under vacuum and the EtOH driven off. Full loss of EtOH was controlled by weight.

NaHCO$_3$, 200 mg, was added to the dry adsorbent with bound nicotine. Fifty mg of the mixture was poured into a non woven polycarbonate fibre tube, 12 mm (in diam.)×24 mm and a pore size of about 250 μm, which was heat welded in one end, and the remaining opened end of the pouch was then also heat welded. The pouches were packed as in Example 1 and 2.

Example 4

Pouches comprising 2 mg nicotine, buffered to about pH 8.3.

This example is identical to Example 3 except for 80 mg nicotine being replaced by the preferred material.

Example 5

Pouches comprising 2 mg nicotine, buffered to about pH 8.6.

This example is identical to Example 3 except for NaHCO$_3$ being replaced by the same amount of Na$_2$CO$_3$.

Example, 6

Nicotine pouches were manufactured according to Example 1. One pouch was administered to two subjects. The subjects were instructed to keep the pouch in the gingival fold in the mouth for 30 minutes, not to suck on it or chew it. After 30 minutes the pouch was withdrawn and analysed for remaining and extracted nicotine by the method described in Example 1.

Results

|  | Rem. nicotine (mg) | Extr. nicotine (mg) | Extr. nicotine (%) |
|---|---|---|---|
| Subject 1 | 1.86 | 0.07 | 3.5 |
| Subject 2 | 1.83 | 0.10 | 5.0 |

The first dose was followed by further 11 hourly doses.

All the pouches were then analyzed and the results are summarized below.

|  | Rem. nicotine (mg) | Extr. nicotine (mg) | Extr. nicotine (%) |
|---|---|---|---|
| Subject 1 | 1.90(1.86–1.95) | 0.03(0–0.07) | 1.53(0–3.48) |
| Subject 2 | 1.81(1.7–1.88) | 0.12(0.06–0.23) | 6.33(2.96–20.6) |

Blood samples were taken during the day and plasma was analyzed for nicotine. All plasma nicotine levels were less than 2 ng/ml.

Example 7

Pouches containing 2 and 4 mg of nicotine were manufactured according to Example 1.

One pouch was administered to two subjects and kept in the gingival fold for different periods of time. The pouches were withdrawn and analysed for nicotine.

Results

| 2 mg | | |
|---|---|---|
| Extr. time (min) | Extr. nicotine (mg) Subj. 1/Subj. 2 | Extr. nicotine (%) Subj. 1/Subj. 2 |
| 5 | —/0.08 | —/4.2 |
| 10 | 0.02/0.03 | 1.1/1.6 |
| 15 | 0.04/0.58 | 2.1/30.2 |
| 20 | 0.06/0.63 | 3.0/32.8 |
| 25 | 0.32/0.55 | 16.4/28.6 |
| 30 | 0.16/0.91 | 8.2/47.4 |

| 4 mg | | |
|---|---|---|
| Extr. time (min) | Extr. nicotine (mg) Subj. 1/Subj. 2 | Extr. nicotine (%) Subj. 1/Subj. 2 |
| 5 | 0.39/0.36 | 10.2/9.4 |
| 10 | 0.38/0.39 | 9.9/10.2 |
| 15 | 0.16/1.05 | 4.2/27.3 |
| 20 | 0.18/0.54 | 4.8/14.1 |
| 25 | 0.18/0.76 | 4.8/19.8 |
| 30 | 0.48/1.5 | 12.5/39.0 |

Example 8

Pouchers containing 4 mg of nicotine were manufactured according to Example 2.

One pouch was administered to one subject and kept in the gingival fold for different periods of time. The pouches were withdrawn and analysed for nicotine.

Results

| Extr. time (min) | Extr. nicotine (mg) | Extr. nicotine (%) |
|---|---|---|
| 30 | 2.09 | 56 |
| 60 | 2.53 | 67 |
| 90 | 3.52 | 94 |

Example 9

Pouches containing 4 mg of nicotine were manufactured according to Example 3.

One pouch was administered to one subject and kept in the gingival fold for different periods of time. The pouches were withdrawn and analysed for nicotine.

Results

| Extr. time (min) | Extr. nicotine (mg) | Extr. nicotine (%) |
|---|---|---|
| 30 | 2.19 | 60 |
| 60 | 2.99 | 81 |
| 90 | 3.57 | 97 |

Example 10

Pouches containing 2 mg of nicotine were manufactured according to Example 4.

One pouch was administered to one subject and kept in the gingival fold for different periods of time. The pouches were withdrawn and analysed for nicotine.
Results

| Extr. time (min) | Extr. nicotine (mg) | Extr. nicotine (%) |
|---|---|---|
| 30 | 0.66 | 38 |
| 60 | 1.04 | 59 |
| 90 | 1.59 | 91 |

Example 11

Pouches containing 2 mg of nicotine were manufactured according to Example 5.

One pouch was administered to one subject and kept in the gingival fold for different periods of time. The pouches were withdrawn and analysed for nicotine.
Results

| Extr. time (min) | Extr. nicotine (mg) | Extr. nicotine (%) |
|---|---|---|
| 30 | 1.04 | 56 |
| 60 | 1.53 | 82 |
| 90 | 1.71 | 91 |

Example 12

One hundred sachet doses of 50 mg total weight, each containing 4 mg nicotine, were prepared by means of the following procedure.

Nicotine (400 mg) was added to 20 ml ethanol and the pH of the solution was adjusted for binding to pH 7.0 by the addition of acetic acid. Then 2.5 g of the preferred material was added to the ethanol-nicotine solution while stirring. After binding, the ethanol and the acetic acid was evaporated under vacuum and moderate heat, 30 C.

In a separate container the same amount (2.5 g) of the preferred material was added to 2.5 ml 0.1 M carbonate buffer in water, pH 8.5, while stirring. This mixture was then air-dried at 50 C over night.

The mixtures were thoroughly mixed and packed into small pouches of non-woven fabric. The pouches were kept in a gas-tight container until used.

Example 13

The heart rate over time was compared when different nicotine preparations were administered to a volunteer nicotine naive male (55 years).

The inventive composition material in a pouch prepared as in Example 12 was administered to the volunteer by placing it under the lip and the heart rate was monitored with a pulse meter. When the heart rate had returned to a normal level and remained constant, a nasal spray (Nicorette®) was administered as two subsequent doses of 0.5 mg nicotine. Similarly, nicotine was administered as a chewing gum (Nicorette®, 4 mg nicotine). The results are shown in FIG. 1.

Figure 1:
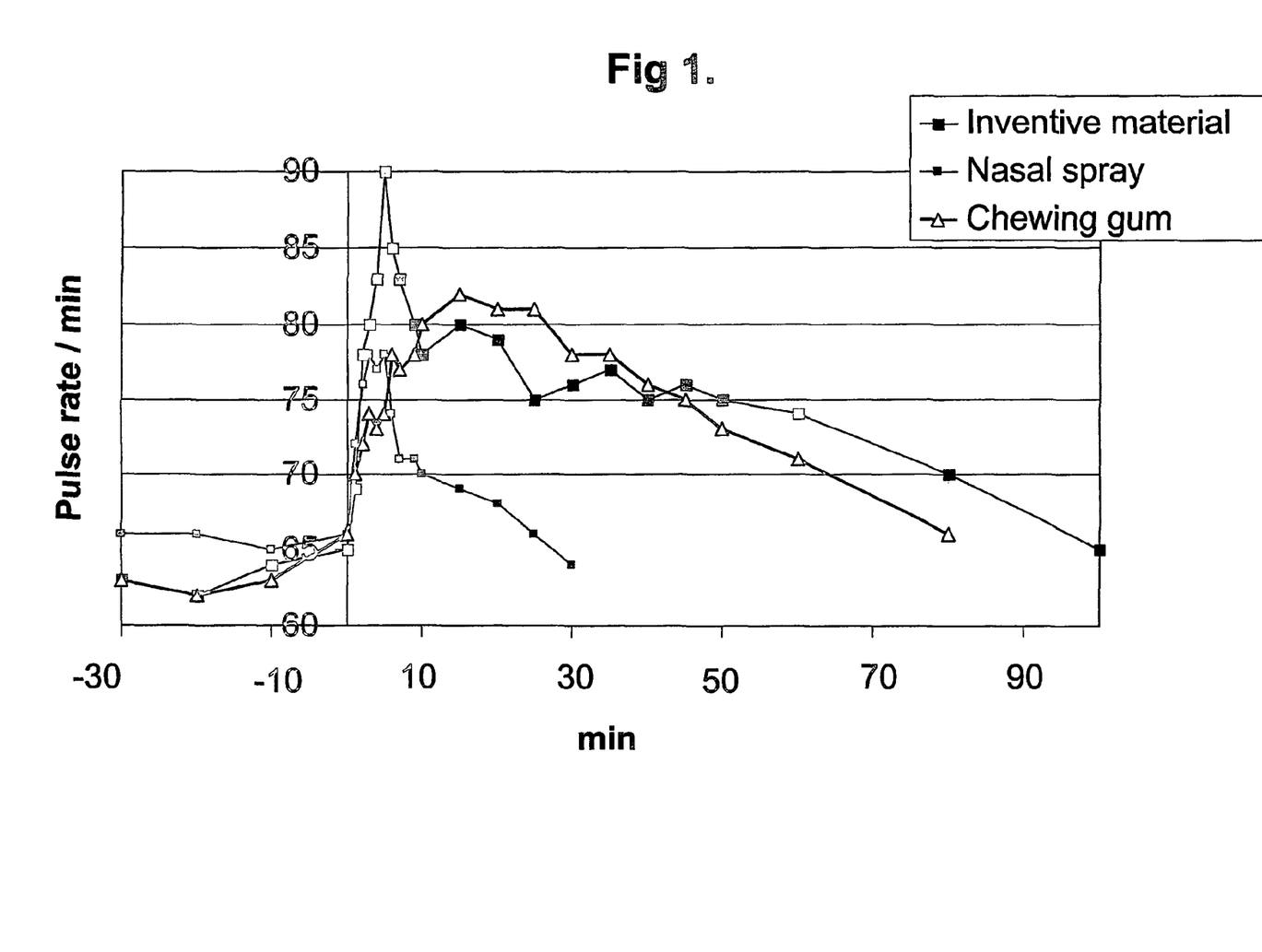
FIG. 1 illustrates the results of Example 13 comparing the inventive material to a nicotine containing nasal spray and a nicotine containing chewing gum.

As shown in FIG. 1, the composition material according to the invention exhibits an immediate effect which is comparable with that of a nicotine nasal spray. In addition, the inventive material results in a prolonged stimulation period effect which is comparable with that of a nicotine chewing gum.

Example 14

An alternative use of the inventive composition material is to include it as carrier of a biologically active substance in a chewing gum.

One hundred doses of 4 mg nicotine/dose were prepared from 95 g of pulverized ordinary peppermint chewing gum, 2.5 g of the preferred inventive material containing 400 mg of nicotine and 2.5 g of fine powdered sodium carbonate. The mixture was thoroughly mixed at 5 C and after a temperature rise to room temperature the chewing gum mass was compressed by extrusion and cut into 1 g pieces. A further formulation alternative with a more enjoyable texture is achieved by coating the pieces.

After a few seconds of chewing a consumer easily recognizes the release of nicotine by a strong nicotine taste throughout the oral cavity.

Example 15

Tablets of 200 mg, containing 4 mg nicotine, were produced by first binding nicotine to the preferred material as in Example 2. The bulk component (lactose) and customary excipients (binder, disintegrant, lubricant etc.) were then added and tablets with 20 mg of the preferred material were then produced in a tabletting machine.

A so formulated nicotine tablet placed in the gingival fold was disintegrated to a powder within minutes.

The effect of the tablet was estimated by monitoring the heart rate in a nicotine naive man. The normal heart rate of 60 increased to 72 after 3 min, indicating that nicotine was released from the tablet.

Example 16

Nicotine (4 mg) was added and bound to 20 mg of the preferred material as in Example 2. A sandwich structure was obtained by first placing the granulate material so produced evenly on a dry flexible composite polymeric "strip-foil" made from a mixture of agarose, starch and gum acacia as well as traditional excipients. An identical "strip-foil", one side of which had been slightly moistened with distilled water, was then placed over the granulate material, and pressure was applied over the sandwich structure for fusing the same. Oval strips of 5 by 10 mm were cut from the sandwich structure, and their remaining moisture was driven off under vacuum at 30° C. The strips were then packed in aluminium Barex® coated envelopes as in Example 1.

A so formulated nicotine strip was placed in the gingival fold of a nicotine naive male and the effect was estimated by monitoring his heart rate. The normal heart rate of 60 increased to 71 after 2 min, indicating that nicotine was released from the strip.

Example 17

The procedure of Example 16 was repeated except for the foils being made from gelatin and added customary excipients.

Similar results were obtained for nicotine release.

Example 18

Pouches comprising 4 mg nicotine and 96 mg of the preferred material were manufactured according to Example 3.

The pouches were added to test tubes and incubated in 5 ml 0.5 M HCl/Carbonate/NaOH buffers at pH 2, 4, 6, 7, 8, and 9 for 30 min at room temperature. The tubes were agitated every 5 min.

The pouches were removed from the tubes and 5 ml toluene was added to each tube. The tubes were again incubated for 30 min at room temperature with agitation every 5 min.

After phase separation the water phase was removed from each test tube and 3 ml 0.5 M HCl was added. The tubes were again incubated with agitation for 30 min as described above.

The water phase was removed and measured spectrophotometrically and the resulting absorbances were plotted against the pH of the extraction buffer.

Different amounts pure nicotine in 2 M NaOH were subjected to same extraction scheme as for the pouches above. The absorbance values obtained were corrected for background absorption originating from pouches without any nicotine. A liner relationship was obtained for a standard curve between absorbance and nicotine up to 9 mg nicotine.

The standard curve was then used to evaluate the results from the nicotine extraction (FIG. 2). At pH 6 and below no nicotine was released, whereas almost all nicotine will be released within 1 h at pH 9.

These results confirm the results of Example 6 and 7, wherein limited amounts of nicotine was released at pH 7. Likewise, the results of Examples 8-11 are also confirmed, a rapid and complete release of nicotine being obtained.

Example 19

Small spherical alginate particles were gelled in calcium chloride, thoroughly washed in distilled water and ethanol dried. Nicotine was then added and bound to the alginate particles as in Example 2 to give 4 mg nicotine per 20 mg particle dose.

Five ml phosphate buffer (0.01 M) of pH 5.0 and pH 9.0, respectively, was added to separate specimens and corresponding extracts were obtained after an incubation of 5 min. The relative concentrations of nicotine in the extracts were determined in a spectrophotometer as the absorbance at 254 nm. The results are shown below.

| pH | $A_{254}$ |
|---|---|
| 5.0 | 0.040 |
| 9.0 | 0.570 |

The results show that nicotine effectively binds to alginate at pH 5 and is desorbed at a higher pH Example 20

Zolmitriptan (200 µl, 1 mg/ml; Zomig®, Nasal spray from Astra Zeneca) was added to specimens of 100 mg of the preferred material, which was subsequently incubated for 10 min. The remaining moisture was then driven off under vacuum.

Distilled water (5 ml) was added to one specimen, and after an incubation of 5 min an extract was obtained, which had a pH of 5. Phosphate buffer, 5 ml, 0.05 M of pH 6 and 7, respectively, was added to other specimens, and corresponding extracts were obtained after an incubation of 5 min.

The relative concentrations of zolmitriptan in the extracts were determined in a spectrophotometer as the absorbance at 280 nm. The results are shown below.

| pH | $A_{280}$ |
|---|---|
| 5.0 | 0.08 |
| 6.0 | 0.67 |
| 7.0 | 0.72 |

The results show that zolmitriptan effectively binds at pH 5 and is desorbed at a higher pH.

The invention claimed is:

1. A composition comprising: a) at least one anionic natural polymeric carbohydrate selected from alginate and xanthan gum, having at least one biologically active substance ionically bound thereto, b) at least one wettable non-soluble polymeric carbohydrate, and c) a pH controlling agent which, in contact with saliva, has a pH that is similar or greater than the pKa of said at least one biologically active substance, said composition provided in a dry form and providing for rapid transmucosal delivery in the mouth of said at least one biologically active substance.

2. The composition according to claim 1, wherein said at least one wettable non-soluble polymeric carbohydrate is a natural carbohydrate.

3. The composition according to claim 2, wherein said natural carbohydrate is cellulose or hemicellulose.

4. The composition according to claim 3, comprising a mixture of pectin, cellulose, and hemicellulose.

5. The composition according to claim 1, wherein said at least one wettable non-soluble polymeric carbohydrate adsorbs, absorbs, or non-specifically binds said at least one biologically active substance.

6. The composition according to claim 1, wherein the composition has a water content of less than 15%.

7. The composition according to claim 1, wherein said pH controlling agent is an ionic carbohydrate.

8. The composition according to claim 1, wherein said pH controlling agent has a charge opposite that of said at least one anionic natural polymeric carbohydrate.

9. The composition according to claim 1, wherein said pH controlling agent is ammonia or a carbonate or phosphate buffer.

10. The composition according to claim 1, wherein said at least one biologically active substance is a protein, a peptide, an alkaloid, a drug for the treatment of migraine, a hypnotic, a sedative, a local anaesthetic, an analgesic, or a drug for the treatment of a psychiatric disorder.

11. The composition material as in claim 10, wherein said peptide is desmopressin, lypressin, oxytocin, nafarelin, buserelin, or a growth hormone.

12. The composition according to claim 10, wherein said alkaloid is nicotine, cotinine, or lobeline, or a derivative or a salt thereof, or caffeine.

13. The composition according to claim 10, wherein said drug for the treatment of migraine is an ergot alkaloid or a $5HT_1$-receptor agonist.

14. The composition according to claim 10, wherein said local anaesthetic is lidocaine or mepivacaine.

15. The composition according to claim 12, wherein said nicotine content is between 0.05 and 6 mg per dose.

16. The composition according to claim 1 in the form of a sheet, discrete pieces, granules, tablets, pills, capsules, lozenges or chewing gum.

17. The composition according to claim 16, wherein said composition is in the form of a sheet and said sheet has a thickness of less than 5 mm.

18. The composition according to claim 16, wherein said composition material is in the form of pieces and said pieces are in the form of a fine mesh gauze.

19. A pouch containing the composition according to claim 1, wherein the pouch is made of a flexible liquid permeable material.

20. The pouch according to claim 19, wherein said flexible liquid permeable material is a fabric.

21. The pouch according to claim 20, wherein said fabric is made of polycarbonate.

22. The pouch according to claim 19, wherein the pouch contains between 0.05 and 1.0 g of said composition.

23. A pouch containing a composition comprising an adsorbent with nicotine ionically bound thereto, the composition, when in contact with saliva, having a pH that is similar or greater than the pKa of said nicotine, said composition provided in a dry form and providing for rapid transmucosal delivery in the mouth of said nicotine, wherein said pouch is flexible and liquid permeable, wherein said adsorbent comprises pectin, cellulose, and hemicellulose, and wherein the content of said nicotine is between 0.05 and 6 mg.

24. The composition according to claim 1, wherein the composition includes less than 10% water.

* * * * *